(12) United States Patent
Spaid et al.

(10) Patent No.: US 7,440,684 B2
(45) Date of Patent: Oct. 21, 2008

(54) METHOD AND APPARATUS FOR IMPROVED TEMPERATURE CONTROL IN MICROFLUIDIC DEVICES

(76) Inventors: Michael A. Spaid, 780 Shary Ave., Mountain View, CA (US) 94041; Andrea W. Chow, 670 Cuesta Dr., Los Altos, CA (US) 94024; Yevgeny Yurkovetsky, 8615 Ava Pl., Apt. 6C, Jamaica Estates, NY (US) 11432; Seth R. Stern, 3779 Redwood Cir., Palo Alto, CA (US) 94306; Allen R. Boronkay, 6981 Polvadero Dr., San Jose, CA (US) 95119; Morten Juel Jensen, 2136 Jones St., San Francisco, CA (US) 94133; Carlton F. Brooks, 715 Pine Ave., San Jose, CA (US) 95125; Ken Swartz, 100 N. Whisman, Apt. 1122, Mountain View, CA (US) 94043

( * ) Notice: Subject to any disclaimer, the term of this patent is extended or adjusted under 35 U.S.C. 154(b) by 306 days.

(21) Appl. No.: 11/323,318

(22) Filed: Dec. 30, 2005

(65) Prior Publication Data
US 2006/0188979 A1     Aug. 24, 2006

Related U.S. Application Data

(63) Continuation-in-part of application No. 10/123,100, filed on Apr. 11, 2002, now abandoned.

(60) Provisional application No. 60/283,527, filed on Apr. 12, 2001.

(51) Int. Cl.
*F24H 1/10* (2006.01)

(52) U.S. Cl. .................................... 392/466; 392/465
(58) Field of Classification Search .................. None
See application file for complete search history.

(56) References Cited

U.S. PATENT DOCUMENTS

| 5,038,852 A | 8/1991 | Johnson |
| 5,270,183 A | 12/1993 | Corbett |
| 5,333,675 A | 8/1994 | Mullis |
| 5,475,610 A | 12/1995 | Atwood |
| 5,508,197 A | 4/1996 | Hansen |
| 5,779,981 A | 7/1998 | Danssaert |
| 5,942,443 A | 8/1999 | Parce |
| 6,042,709 A | 3/2000 | Parce |
| 6,153,073 A | 11/2000 | Dubrow |

(Continued)

FOREIGN PATENT DOCUMENTS

WO        WO 00/05642        8/2000

(Continued)

*Primary Examiner*—Thor S Campbell
(74) *Attorney, Agent, or Firm*—Cardinal Law Group

(57) ABSTRACT

A microfluidic system and method for employing it to control fluid temperatures of fluids residing within microchannels of a microfluidic device. The microfluidic device is provided with a top layer and a bottom layer and microchannels configured therebetween. Temperature of the fluid within the microchannels is controlled in various ways including the use of electrical resistive heating elements and by providing zones located in contact with the top and bottom layers of the microfluidic device for circulating heat transfer of fluid therein.

17 Claims, 3 Drawing Sheets

U.S. PATENT DOCUMENTS

| | | |
|---|---|---|
| 6,235,471 B1 | 5/2001 | Knapp |
| 6,440,706 B1 | 8/2002 | Vogelstein |
| 6,503,750 B1 | 1/2003 | Benett |
| 6,787,338 B2 | 9/2004 | Wittwer |
| 6,901,217 B2 * | 5/2005 | Gamboa et al. ............. 392/484 |
| 7,049,558 B2 * | 5/2006 | Baer et al. .................. 219/548 |
| 7,090,001 B2 * | 8/2006 | Zhou et al. ............. 165/104.21 |
| 7,139,172 B2 * | 11/2006 | Bezama et al. .............. 361/699 |
| 2003/0116552 A1 * | 6/2003 | Santoruvo et al. ........... 219/209 |
| 2003/0213580 A1 * | 11/2003 | Philpott et al. ................ 165/46 |
| 2005/0092477 A1 * | 5/2005 | Philpott et al. .............. 165/185 |
| 2006/0083496 A1 * | 4/2006 | Kylberg et al. .............. 392/418 |

FOREIGN PATENT DOCUMENTS

| | | |
|---|---|---|
| WO | WO 02/22878 | 3/2002 |
| WO | WO 2005/094981 | 5/2005 |

* cited by examiner

METHOD AND APPARATUS FOR IMPROVED TEMPERATURE CONTROL IN MICROFLUIDIC DEVICES

CROSS REFERENCE TO RELATED APPLICATIONS

This application is a continuation-in-part of U.S. patent application Ser. No. 10/123,100, which was published on Dec. 26, 2002 as US 2002/0197630, and which is incorporated herein by reference. That application claims priority to and benefit of U.S. Provisional Patent Application 60/283,527, which was filed on Apr. 12, 2001, and which is incorporated herein by reference.

STATEMENT REGARDING FEDERALLY SPONSORED RESEARCH OR DEVELOPMENT

The present invention was made with government funding from the United States National Institute of Standards and Technology (NIST), through the Advanced Technology Program (ATP) under Grant No. 70NANB8H4000, and the United States government has certain rights in the invention.

TECHNICAL FIELD

The present invention is directed to microfluidic devices commonly employed in areas such as biotechnology, genetic research, DNA diagnostics and automated high-speed thermocycling. In each instance, careful temperature control is critically important and the present invention provides various physical embodiments and methods for providing such control.

BACKGROUND OF THE INVENTION

There has been a growing recognition that microfluidic devices have a wide range of applicability in the areas of biotechnology, genetic research, DNA diagnostics and thermocycling for carrying out temperature controlled processes. Of particular applicability is the amplification of DNA sequences through polymerase chain reactions (PCR). PCR replicates small amounts of DNA in a series of heating and cooling cycles and has been used in diverse research applications including biology, DNA sequencing, cloning, research, and genetic synthesis using published DNA sequences. Microfluidic devices also provide means for monitoring and controlling a wide variety of process parameters using resistivity and/or conductivity measurements.

Microfluidic systems comprise microfluidic devices or "chips" that have channels that are generally fabricated at the microscale, that is, having at least one channel cross sectional dimension (e.g., channel depth, width, or radius) of less than 1 mm, and typically in the range of from about 0.1 micrometers to about 500 micrometers. Planar chip technology employed in fabricating such devices is disclosed in Manz et al., Trends in Analytical Chemistry (1990) 10(5):144-149 and Manz et al., Advances in Chromatography (1993) 33:1-66. These references describe the fabrication of microfluidic devices and particularly microcapillary devices composed of silicon and glass substrates. It is well known that such devices can be employed for carrying out capillary electrophoresis, liquid chromatography, flow injection analysis, chemical reactions and synthesis.

Not surprisingly, chemical and biological analyses carried out in microfluidic devices require precise control over process parameters and, specifically, process temperatures. Biological reactions, as well as chemical reactions, generally, are exceedingly temperature sensitive requiring not only the ability to rapidly change processing temperatures during various stages of the chemical or biological processes but further require temperature uniformity from microchannel to microchannel. However, providing such temperature control and uniformity has proven to be a formidable challenge that those involved in this technology have yet to fully resolve.

Commonly, electrical energy has been employed to heat fluids contained within microfluidic channels. For example, in U.S. Pat. No. 5,965,410, the disclosure of which is incorporated herein by reference, electric current is applied through the fluids themselves. This technique has been employed successfully for a wide variety of chemical and biological applications, such as PCR. This global strategy can be fine tuned by directing electrical current through only portions of fluid-filled microchannels in order to selectively elevate temperature as processing parameters dictate.

In addition to the "Joule" heating described in referenced U.S. Pat. No. 5,965,410, fluid heating can be carried out by employing conventional heating mechanisms including the use of external heating elements such as hot plates or Peltier devices placed adjacent to the microfluidic channels to cycle the temperature of fluids contained therein. In addition, as described in co-pending U.S. application Ser. No. 10/123,100, resistive heaters in the form of longitudinally extending metallic filaments can be fabricated on the surface of a microfluidic device adjacent to the various microfluidic channels. As an electric current passes through the longitudinally extending metal films, heat is generated which is transferred directly to fluids contained within nearby microfluidic channels.

In order to gain further appreciation of microfluidic devices of the type referred to herein, reference is made to FIG. 1. FIG. 1 is a schematic example of a microfluidic channel network including body structure 2 that includes channel network 4 disposed therein. The microfluidic device also includes external sample accession capillary element or pipettor (not shown) that enters the device through an interface 6. The pipettor extends from the body of the microfluidic device so that materials can be brought into the channel network from sources external to the device itself, for example, from multiwell plates.

Channel network 4 also includes common channel 10 that receives materials drawn into the network from the pipettor element. This common channel is fluidly connected to a plurality of separate analysis channels 12-26. The analysis channels are used to perform different assays on separate aliquots of the sample material drawn into the sample network. The number of different analysis channels typically depends upon the desired rate of throughput for the overall system, and for each channel network incorporated in that system. Typically, a given channel network will include between about 1 and 20 separate analysis channels, and preferably between 5 and 15, with 8 to 12 analysis channels being most preferred.

Continuing reference to FIG. 1, each analysis channel typically is fluidly connected to a source of reagents, for example, reservoir 28 that may include either locus or patient specific reagents. Each analysis channel typically includes at least one, and often several, heating zones, for example, zones 26a and 26b, for carrying out different desired operations within the analysis channel. By way of example, within region 26a, an amplification reaction is optionally carried out to amplify the section of the patient's genomic DNA that includes the particular polymorphic locus. This is generally accomplished by combining the patient's DNA with appropriate amplification reagents, for example, primers, polymerase and dNTPs, followed by thermally cycling the contents of the channel, for example, within region 26a, through melting, annealing and extension processes, until sufficient amplified product has been produced.

As noted above, heating the fluid contained with the channels passing through region 26a can be carried out using electrical current supplied by electrodes in electrical contact with opposite ends of a suitable heating agent, such as the longitudinally extending metal films 30 (only one designated), or the fluid in the channel in the case of Joule-heating. Heat is then generated by applying current through the metal films 30 or the fluid in region 26a until the fluid in the channels in that region reaches the desired temperature. The process of Joule heating is described in detail in U.S. Pat. No. 5,965,410. Examples of metal films used as resistive heaters include those described in U.S. Pat. No. 6,132,580, the disclosure of which is incorporated by reference herein. Alternatively, conventional heat mechanisms may be employed, including the use of an external heating element, for example, a hot plate or a Peltier device, placed adjacent to the heating region to cycle the temperature therein.

FIG. 1 illustrates one embodiment of the use of resistive heaters for temperature control of multiple analysis channels. The resistive heaters can comprise multiple thin resistive metal films, shown as dotted lines, for example, 30, deposited on both sides of each analysis channel in region 26a. The resistive heaters are connected to electrical leads for the application of a voltage across the metal film. Current applied through the metal film heats the contents of the channels disposed therebetween. Temperature sensors can be incorporated into devices in accordance with the invention for measuring temperature within the heated region of the channel network. In the embodiment shown in FIG. 1, the temperature sensors comprise resistance thermometers that include material having an electrical resistance proportional to the temperature of the fluids contained within the microchannels.

In addition to the need to apply controlled amounts of energy to fluids contained within microchannels in order to elevate their temperatures, it is also necessary to provide means to cool such fluids to further control processing conditions. For example, reference was made previously to the use of such devices in carrying out PCR cycling. Such cycling requires the steps of denaturation, primer annealing and DNA synthesis. During denaturation, the starting mixture is first heated to about 95° C. for separating the double strands of DNA. After denaturation of the DNA, the mixture is cooled to about 55° C. to allow the primers to bind to their complimentary sequences on separated strands. Thereupon, the mixture is heated to a temperature of about 72° C. so that the DNA polymerase catalyzes the extension of the annealed primers on the template strand.

Although commercially available apparatus has been employed in carrying out the PCR cycling protocol, microfluidic devices such as those shown in FIG. 1 are particularly well adapted for doing so. However, again, PCR cycling requires exacting precision to uniformly and accurately raise and lower the temperature of the fluids contained within the subject microchannels as processing conditions so dictate. Furthermore, it is advantageous for the transitions in temperature between the temperatures required for denaturation, primer annealing and DNA synthesis occur as rapidly as possible.

It is intuitively obvious that in employing a microfluidic device such as that shown in FIG. 1 having parallel processing channels employed in carrying out, for example, in-line PCR manipulation, every reaction channel must produce equivalent thermal profiles. However, the tendency has been to increase channel density within such microfluidic devices, which, in turn, increases the amount of power delivered to such devices. Without adequate removal of heat, "hot spots" on the microfluidic chips can form resulting in thermal gradients between reaction channels. In this regard, reference is made to FIG. 2, which graphically displays the normalized average temperature for nine parallel microfluidic channels that are equally spaced, like the eight parallel channels in region 26a of FIG. 1, and heated by Joule heating. The temperature is scaled such that the collective average temperature $T_{ave}$ of all nine channels equals one. Significant temperature differences between channels become measurable, particularly as channel-to-channel spacing is reduced. This is not particularly surprising since one channel would have a tendency to transfer energy to adjacent parallel channels, particularly as spacing between channels diminishes. The channels on the edges of the group of parallel channels, such as the channel numbers 1 and 9, tend to be cooler than the interior channels because those outer channels only have one adjacent channel. The temperature of the interior channels even varies, with interior channels closer to the edge tending to be cooler. Variation of channel temperatures can be dramatic, as much as 30° C. across the various parallel microchannels when operating at set points of 95° C. Although this effect can be diminished by using individually controllable power supplies to heat each channel, the resulting complexity in equipment and fabrication costs make such an approach undesirable.

It is also of critical importance that any such microfluidic device possesses the ability to controllably remove thermal energy from the device and thus fluids contained therein. For example, in using such devices to carry out PCR reactions, it is necessary that fluids contained within the microchannels be maintained at temperatures of approximately 95° C., 72° C. and 60° C., so some of the temperature transitions require removal of heat from the microfluidic device. The present invention teaches techniques for doing so, including applying fluids directly against the microfluidic chip surfaces, which can be employed to effectively introduce and withdraw thermal energy. When used in conjunction with other aspects of the present invention, the details of which will be disclosed hereinafter, one is able to achieve a device capable of microfluidic manipulation with a degree of temperature control that has heretofore been unavailable.

It is thus an object of the present invention to provide a microfluidic device capable of controlling thermal energy applied to and withdrawn from fluids being manipulated therein.

It is yet a further object of the present invention to provide a microfluidic device having multiple channels for carrying fluids therein in which the thermal energy and thus temperature within each channel is capable of being controlled and maintained consistent with temperatures of fluids in companion channels.

These and further objects will be more readily appreciated when considering the following disclosure and appended claims.

SUMMARY OF THE INVENTION

The present invention involves a microfluidic system comprising a microfluidic device and a method for using it wherein the temperatures of fluids within the channels of the microfluidic device are controlled to a degree unachievable heretofore. Heat transfer fluids can be applied to the top and/or bottom layers to promote heat transfer. In addition, the geometry of the microchannels and heat generating expedients such as metal traces for carrying heat generating electric current are configured in such a way as to promote uniformity of fluid temperatures within the plurality of microchannels contained within such devices.

DETAILED DESCRIPTION OF THE INVENTION

There has been a growing recognition that microfluidic systems comprising microfluidic devices have a unique place in carrying out a number of operations such as PCR for DNA amplification. For example, PCR by temperature cycling is the amplification method that is used for target nucleic acid amplification. It is critical in carrying out such operations that the temperature of fluids within the channels in a microfluidic device be controllable such that temperature profiles be uniform within channels and among different channels, and be capable of being altered at the direction of an operator.

To heat fluids within the channels of a microfluidic device in a designated heating region (e.g. region 26a of FIG. 1), thermal energy can be generated in heating elements adjacent to the channels in the heating region by passing electrical current through those elements. Heat is generated by increasing current through the elements until the desired temperature is achieved. This process is described in detail in U.S. Pat. No. 5,965,410, which is incorporated herein by reference. Alternatively, fluids contained within such channels can be heated by applying an electric current through the fluid itself, such a process, known as Joule heating, is described in U.S. patent application Ser. No. 60/269,245, filed on Feb. 15, 2001, which is incorporated herein by reference. Further, the prior art has taught the use of conventional heating mechanisms such as hot plates and Peltier devices placed adjacent to the heating region to cycle temperatures. Resistive heaters have also been used including those described in U.S. Pat. No. 6,132,580, which is incorporated herein by reference.

Figure 1:
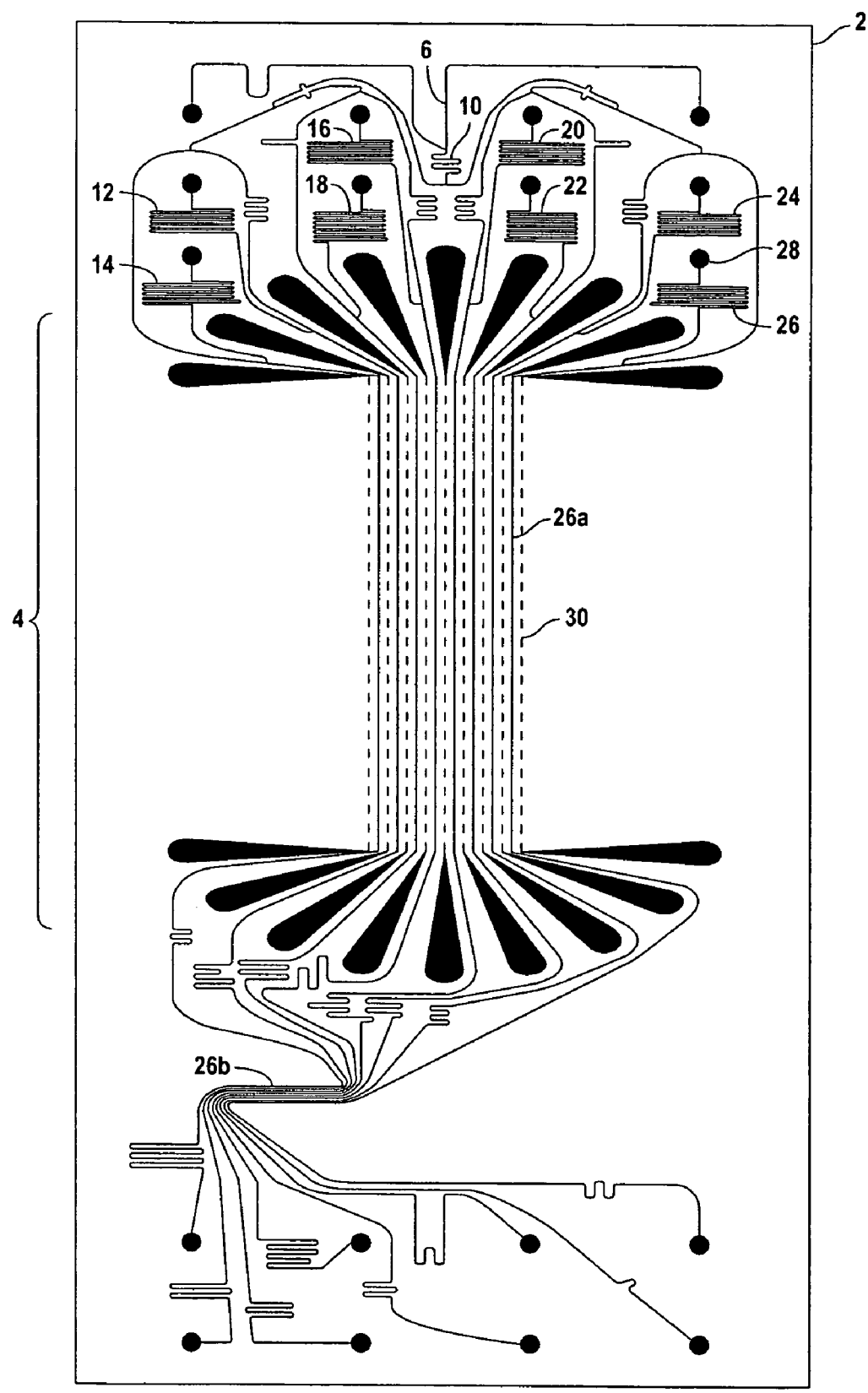
FIG. 1 is a schematic representation of a microfluidic system particularly showing the microfluidic channels and heating means employed.

Embodiments of the invention are directed toward providing the temperature control and uniformity required to carry out temperature-dependent processes, such as PCR, in a plurality of channels on a microfluidic device. For example, such devices generally embody multiple channels for carrying processing fluids in parallel. When thermal energy is applied to each channel in a plurality of parallel channel, fluids contained within the centrally located channels tend to reach higher temperatures than fluids contained within edge channels. Thermal energy is applied to each channel when, for example, the fluid in the channel is joule heated, or when each channel has one or more heating elements associated with it. So the channels in region 26a of FIG. 1 are each heated because each channel is surrounded by two resistive heating elements 30. It is surmised that centrally located channels in a parallel array of individually heated channels receive thermal energy from adjacent channels, while channels on the edge are more exposed to the ambient surroundings. Although such effects could be minimized by increasing spacing between channels as well as independently driving each metal trace with its own power supply, or joule heating the fluid in each channel with an individual power supply, such "solutions" to the temperature uniformity problem have not been embraced by fabricators of such devices. Increased channel spacing results in the loss of fluid processing capacity in a device, while providing separate power supplies for individual metal traces or channels would greatly increase the complexity of such devices and increase fabrication costs.

Figure 2:
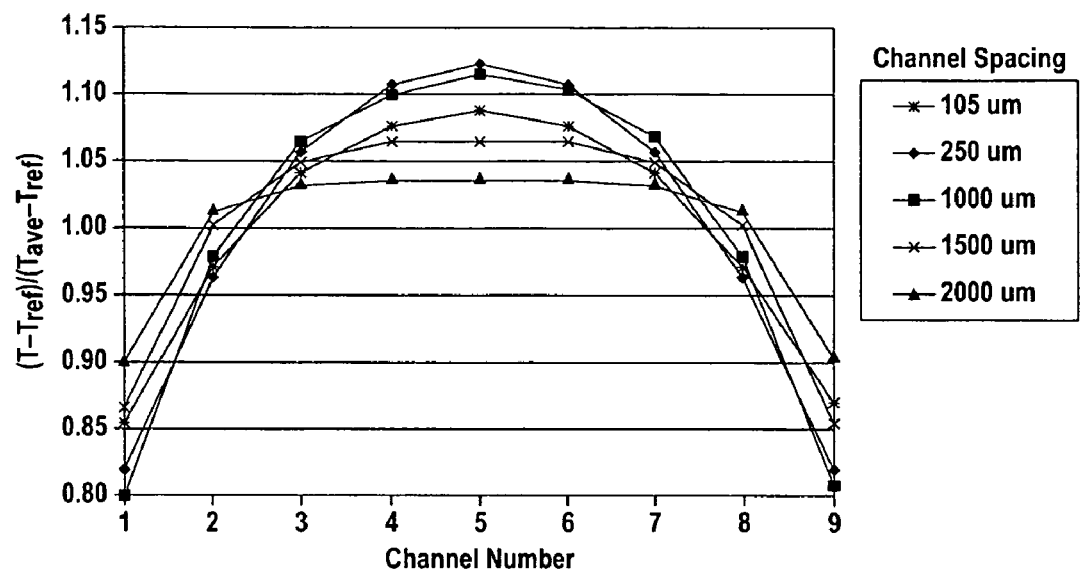
FIG. 2 is a graphical depiction of the temperature variation among parallel channels in a microfluidic device.

The present invention recognizes that for parallel processing of samples with an in-line PCR microfluidic device, every reaction channel on the chip should produce equivalent thermal profiles. But, as the number of parallel PCR reaction channels on the chip increases, the amount of thermal energy delivered to the device also increases. Without the adequate removal of heat, "hot spots" on the chip form that result in thermal gradients between reaction channels as shown graphically in FIG. 2. FIG. 2 depicts the normalized average temperature for each of nine parallel microfluidic channels that are joule heated using identical electric currents. The temperature is scaled such that the average $T_{ave}$ equals one. As shown, significant temperature differences exist among the channels, particularly as channel-to-channel spacing is reduced. In fact, it has been observed that variations in channel temperature can be quite dramatic, on the order of approximately 30° C. for channels in which a set point of 95° C. had been established.

Figure 5A:
FIG. 5a is a cross-sectional depiction of a typical channel configuration embedded within a microfluidic system.
Figure 5B:
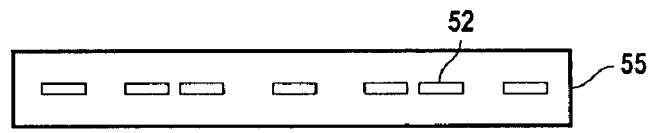
FIG. 5b is a cross-sectional view of a microfluidic system altered from that shown in FIG. 5a for achieving improved uniform fluid temperatures.
Figure 7:
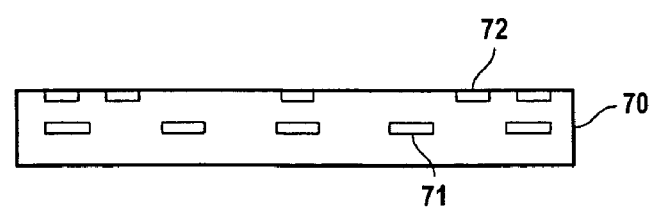
FIG. 7 is a side cross sectional view of yet another embodiment of the present invention depicting a unique relationship between channel spacing and the spacing of companion metal traces to enhance channel to channel temperature uniformity.

A first embodiment of the invention, which enhances channel-to-channel temperature uniformity, is shown in FIGS. 5a, 5b and 7, which show a cross-sectional view of a microfluidic device. As noted, when channels 51 are evenly spaced within microfluidic chip 50 (FIG. 5a), heat transferred to the inner channels cannot dissipate to the extent that heat dissipation is observed in the outer channels. Thus, heat or thermal energy provided to the inner channels is shared with adjacent parallel channels thus raising their temperatures above those temperatures observed in outer channels. This phenomenon can be ameliorated by judicially spacing channels unevenly such as is shown in FIG. 5b. Specifically, it is noted that channels 52 contained within chip 55 are arranged such that the outer channels are closer to one another than the spacing of the inner channels. Thus, outer channels 52 would tend to share thermal energy to a greater degree than the inner channels and by judiciously selecting appropriate channel spacing, channel-to-channel temperatures can be substantially equalized.

Appropriate results can also be achieved by not only creating non-uniform spacing between channels (FIG. 5b), but also by establishing non-uniform spacing between metal traces. In this regard, reference is made to FIG. 7 wherein chip 70 containing equally spaced microfluidic channels 71 is heated by embedded metal traces 72 such as those taught in the '410 patent. In this regard, however, metal traces 72 are unevenly spaced such that the metal traces are positioned closer together proximate the edges of chip 70 while, at the center of chip 70, the density of metal traces is reduced. As such, more thermal energy is transferred to channel 71 proximate the edges of chip 70 to, again, achieve uniform heating of fluids contained within channels 71.

Figure 4:
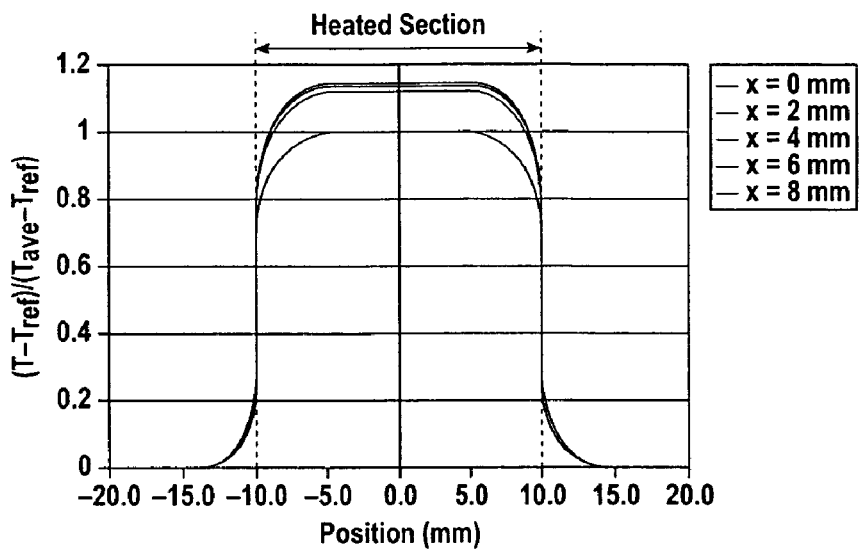
FIG. 4 is a graphical depiction of temperature profiles of fluids contained within channels evidencing the "end effects" typical of microfluidic systems, generally.
Figure 6:
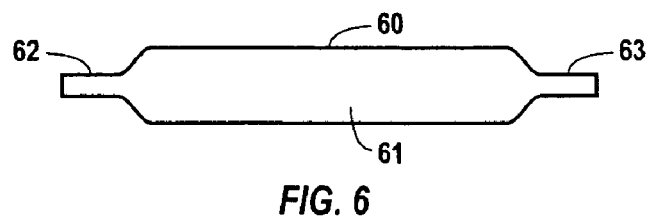
FIG. 6 is a side plan view of yet another embodiment of the present invention exhibiting revised channeled geometry to compensate for end effects.

Further, it has been recognized that "end effects" can cause variation in temperature along the longitudinal axis of a channel that is heated by joule heating or by a heating element that extends in a direction parallel to the channel. Such "end effects" are graphically depicted in FIG. 4, which shows a channel temperature profile along the length of the channel. The temperature profile shown in FIG. 4 shows such "end effects" that extend for a few millimeters on either side of the heated section of the microfluidic chip. In the example shown in FIG. 4, the heated section extends from minus ten to plus ten millimeters on the longitudinal axis of the chip. The temperature of the portions of the channel within the heated region that are near the edges of the heated region are not at the same temperature as the portion of the channel near the center of the heated region. In order to minimize these "end effects," channels configured as in FIG. 6 produce even heating throughout their longitudinal axes. FIG. 6 shows a cross-sectional view of the channel along the entire section of the channel extending through the heated region. Note that cross-sectional view in FIG. 6 is generally perpendicular to the cross-sectional views in FIGS. 5a, 5b, and 7, which show cross-sectional views of channels along their width. In FIG. 6, channel 60 is shown having a non-uniform profile wherein a central portion beneath heated section 61 is wider (or deeper) than channel portions 62 and 63 at the ends of the heated section of the channel. Without being bound by any specific theory of operation, it is believed that such a channel geometry results in more even heating along longitudinal axis of each channel by having less fluid within narrowed channel sections 62 and 63 as compared to wider region 61. As such, at the ends of channel 60, the heating energy is concentrated on a smaller cross section of fluid, which tends to increase the heat applied to the fluid in the smaller cross sectional areas.

Although the thrust of the present invention to this point has been to suggest various embodiments for creating temperature uniformity within channels and from channel to channel, it is envisioned that in some applications, it may be preferable to extend the teachings of the present invention in order to intentionally create "hot spots" or non-equal temperature regions in order to facilitate a particular process. For example, the channel profile as shown in FIG. 6 could be exaggerated to create a heated zone in narrowed region 63 in the event that a fluidic enzyme requires a "hot start." For example, the channel could be purposely narrowed to allow it to achieve the higher temperature required to "hot start" the PCR reaction before the reaction mixture enters a main reaction channel.

When a microfluidic system must subject fluid in microfluidic channels to a repetitive cycle of temperatures, such as when the fluid is thermocycled to enable PCR, it is important to provide a protocol for cooling the fluid in the channels. Vapor compression heat pumps and Peltier devices that could be used to cool microfluidic channels can cause temperature differentials between various surfaces of a microfluidic device, may not provide rapid enough cooling, and may not provide for localized temperature control.

Thus, embodiments of the present invention provide an efficient means of cooling, as well as heating a microfluidic chip that can be employed alone or with either metalized or Joule heating protocols. In this regard, reference is made to FIG. 3. Specifically, fluids, such as water, alone or with a glycol, or a gas such as air or nitrogen can be maintained at predetermined and selected temperatures within reservoirs 33, 34 and 35. In the case of PCR, reservoirs 33, 34 and 35 can be maintained at approximately 95° C., 72° C. and 60° C. One or more of these temperature-controlled fluids are directed to supply valve 33 and feed line 38 entering cartridge base 41 at input 43. These temperature controlled fluids enter flow region 42, which is defined by the backside 49 of the microfluidic device 39, a sealing means such as an o-ring or gasket, and the cartridge base 41. When the fluid flows through flow region 42, it directly contacts the backside 49 of chip 39. The appropriate fluid from reservoirs 33, 34 and 35 is selected from supply valve 32 by pumps (not shown) from the three constant-temperature reservoirs of fluid. The fluid flowing through flow region 42 exits the flow region through output 44 of cartridge base 41. At that point, the fluid flows through feed line 37 into return valve 31, which directs it back into one of the reservoirs 33, 34 and/or 35. Although not shown, fluid could contact top layer 48 of chip 39 by duplicating the structure comprising the cartridge base 41 and flow region 42 on the topside of the chip. Applying heating or cooling fluid directly against both the topside 48 and the backside 49 of the microfluidic device 39 would further enhance temperature uniformity within the device, and provide more responsive temperature control.

Although not shown, it is quite apparent that fluid transfer between reservoirs and the microfluidic device can be computer controlled, the implementation of which would be obvious to anyone skilled in this art. Further, it is envisioned that as a preferred embodiment, each of reservoirs 33, 34 and 35 can be maintained as a closed plumbing loop such that fluid leaving region 42 be returned to the same reservoir from which it originated. In this way, maintaining the temperatures within the reservoirs can be done in a very cost efficient fashion.

Figure 3:
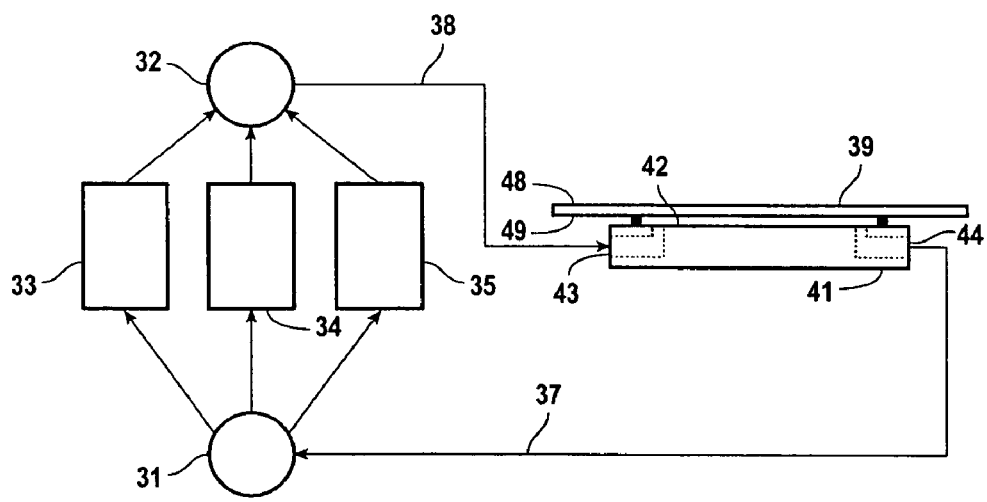
FIG. 3 is a schematic depiction of an embodiment of the present invention employed to effectively carry out heat transfer within fluids of a suitable microfludic system of the present invention.

The embodiment depicted in FIG. 3 offers a number of advantageous features. It is noted that because the various temperature control fluids are applied directly against the top and/or bottom layers 48 and 49 of chip 39, thermal resistance between the fluids and the chip is very low and repeatable, varying only with flow rate and pressure, which can be accurately controlled, and system geometry which is, of course, constant. When the temperature of the chip is changed, there are no large temperature gradients in the chip after the transient. This means that the microfluidic channel temperatures will be substantially the same as the fluid temperature after the transient. Since the fluid temperature is easy to measure at the entrance to the chip surface (such as at 43), it is relatively easy to achieve accurate chip temperatures. Fluids such as water exhibit high heat capacities, while the microfluidic device tends to have a small thermal mass, meaning that fluid temperatures will change little as the fluid flows across chip 39 within region 42 leading to very uniform temperatures within the processing zone of the chip.

As noted previously, the application of cooling or heating fluid directly against the surfaces of a chip can be carried out in conjunction with the use of metal traces, Joule heating or other known means for transferring thermal energy to fluids contained within the microchannels of such chips. However, the embodiment of FIG. 3 can also be employed to the exclusion of traditional thermal energy generators. The advantages of doing so are quite apparent. Specifically, if the embodiment of FIG. 3 is employed to the exclusion of other means of heating chip 39, metallization and related manufacturing costs can be eliminated thus reducing chip costs and complexity. Further, the reaction zone within the chip can be made much smaller than corresponding chips having internal resistive heating. It is hypothesized if heating (and cooling) is conducted through the application of a fluid against outer layers of the chip, a manufacturer could easily configure four 12-channel chips on a single plate far exceeding current chip density.

Although it was suggested that reservoirs 33, 34 and 35 be maintained at the traditional "PCR temperatures," the embodiment of FIG. 3 may not be so restricted. As one skilled in the art would recognize, it may be necessary to maintain the fluids at slightly different temperatures that the traditional PCR temperatures in order to achieve the desired PCR temperatures within the channels of the microfluidic device. In another alternative embodiment, temperature transition times could be reduced by maintaining one reservoir at an extremely high temperature, such as 120° C., and a second at a low temperature, for example, 20° C. Thus, when a fast temperature increase is desired, the "extra hot" temperature fluid is flowed across the chip temporarily followed by fluid of the desired temperature. As such one might run 120° C. fluid for one second followed by 95° C. fluid for the rest of the PCR denaturization portion of the PCR cycle. Similarly, an "extra cold" fluid can be employed when rapid cooling is desired. In either case, traditional metal traces or Joule heating can be employed in conjunction with the embodiment of FIG. 3. The electric heating elements could be employed to speed up temperature increases, while final temperatures would be maintained by heat transfer fluids. Metal traces or other electrical heating elements can be placed on side of the chip, such as on top layer 48 while the appropriate heat transfer fluid within region 42 to bottom layer 49 of chip 39.

In yet a further variation of the protocol shown in FIG. 3, valving could be simplified by providing two separate fluid systems, one on each side of chip 39. One side could be made to run only "cold" fluid, for example, at 60° C. while the other side could run only "hot" fluid at, for example 95° C. Fluids could be pumped against top layer 48 or bottom layer 49 depending upon which temperature is desired. For a three temperature cycling process, both sides could be run at the same time, possibly at different flow rates to achieve different final temperatures in the microfluidic channels.

In yet a further variation, various components of the system shown in FIG. 3 could be made small enough to fit within the body of a microfluidic device. This would greatly reduce the possibility of fluid leakage. It is also contemplated that a single fluid loop could be employed in which fluid temperature is changed "on the fly" rather than using multiple separate fluid supplies such as reservoirs 33, 34, and 35 held at different temperatures.

The invention claimed is:

1. A method of controlling temperature of fluids residing within microchannels of a microfluidic device, said microfluidic device having a top layer and a bottom layer and microchannels configured therebetween, said microfluidic device further comprising a plurality of reservoirs of heat transfer fluid, each reservoir being maintained at a controlled temperature, said method comprising flowing heat transfer fluid from one or more of said reservoirs to said top layer or said bottom layer or to both said top and bottom layers of said microfluidic device.

2. The method of claim 1 wherein said heat transfer fluid comprises a member selected from the group consisting of water, glycol, air and mixtures thereof.

3. The method of claim 1 wherein such heat transfer fluid is circulated from its own reservoir to said microfluidic device and back to said own reservoir.

4. The method of claim 1 wherein said heat transfer fluid is maintained in three reservoirs.

5. The method of claim 4 wherein said heat transfer fluid within said three reservoirs is maintained at temperatures of approximately 95° C., approximately 72° C. and approximately 60° C. respectively.

6. The method of claim 1 wherein said heat transfer fluid is applied to outer surfaces of said top and bottom layers.

7. The method of claim 1 wherein said heat transfer fluid of the same temperature is applied to said top and bottom layers.

8. The method of claim 1 wherein said heat transfer fluid of different temperatures is applied to said top and bottom layers.

9. The method of claim 1 wherein said fluids residing within said microchannels are further heated by applying a selectable electric current through said fluid in at least a portion of said microchannels, said fluid contained within said portion of said micro channels having an electrical resistance.

10. The method of claim 1 wherein at least one of said microchannels is configured with an electrically resistive heating element.

11. The method of claim 10 wherein power is selectively applied to said electrically resistive heating element for controllably raising the temperature of said fluids within said at least one of said microchannels.

12. A method of controlling temperature of fluids residing within microchannels of a microfluidic device, said microfluidic device having a top layer and a bottom layer and a plurality of substantially parallel microchannels configured therebetween, said method comprising controlling temperature of said fluids residing within said microchannels by creating non-uniform spacing between said plurality of microchannels to enhance uniformity of temperature of said fluids residing within said plurality of microchannels.

13. The method of claim 12 wherein temperature of said fluids residing within said microchannels of said microfluidic device is further controlled by applying heat transfer fluid to said top layer or said bottom layer or to said top and bottom layers of said microfluidic device.

14. A method of controlling temperature of fluids residing within microchannels of a microfluidic device, said microfluidic device having a top layer and a bottom layer and a plurality of substantially parallel microchannels configured therebetween and electrically resistive heating elements associated with said plurality of microchannels for transferring energy to said fluids residing therein, said method comprising controlling temperature of said fluids residing within said microchannels by creating non-uniform spacing between said electrically resistive heating elements to enhance uniformity of temperature of said fluids residing in said plurality of microchannels.

15. The method of claim 14 further comprising applying heat transfer fluid to said top layer or to said bottom layer or to both said top and bottom layers of said microfluidic device.

16. A method of controlling temperatures of fluids residing within microchannels of a microfluidic device, said microfluidic device having a top layer, bottom layer, longitudinal axis and a plurality of substantially parallel microchannels, each microchannel having a longitudinal axis configured therebetween and parallel to said longitudinal axis of said microfluidic device, said method comprising controlling temperature of said fluids residing within said microchannels by creating non-uniform channel dimensions along said longitudinal axis.

17. The method of claim 16 further comprising applying heat transfer fluids to said top layer or to said bottom layer or to both said top and bottom layers of said microfluidic device.

* * * * *